May 2, 1950 H. C. SWIM Plant Pat. 938
ROSE PLANT
Filed March 8, 1949
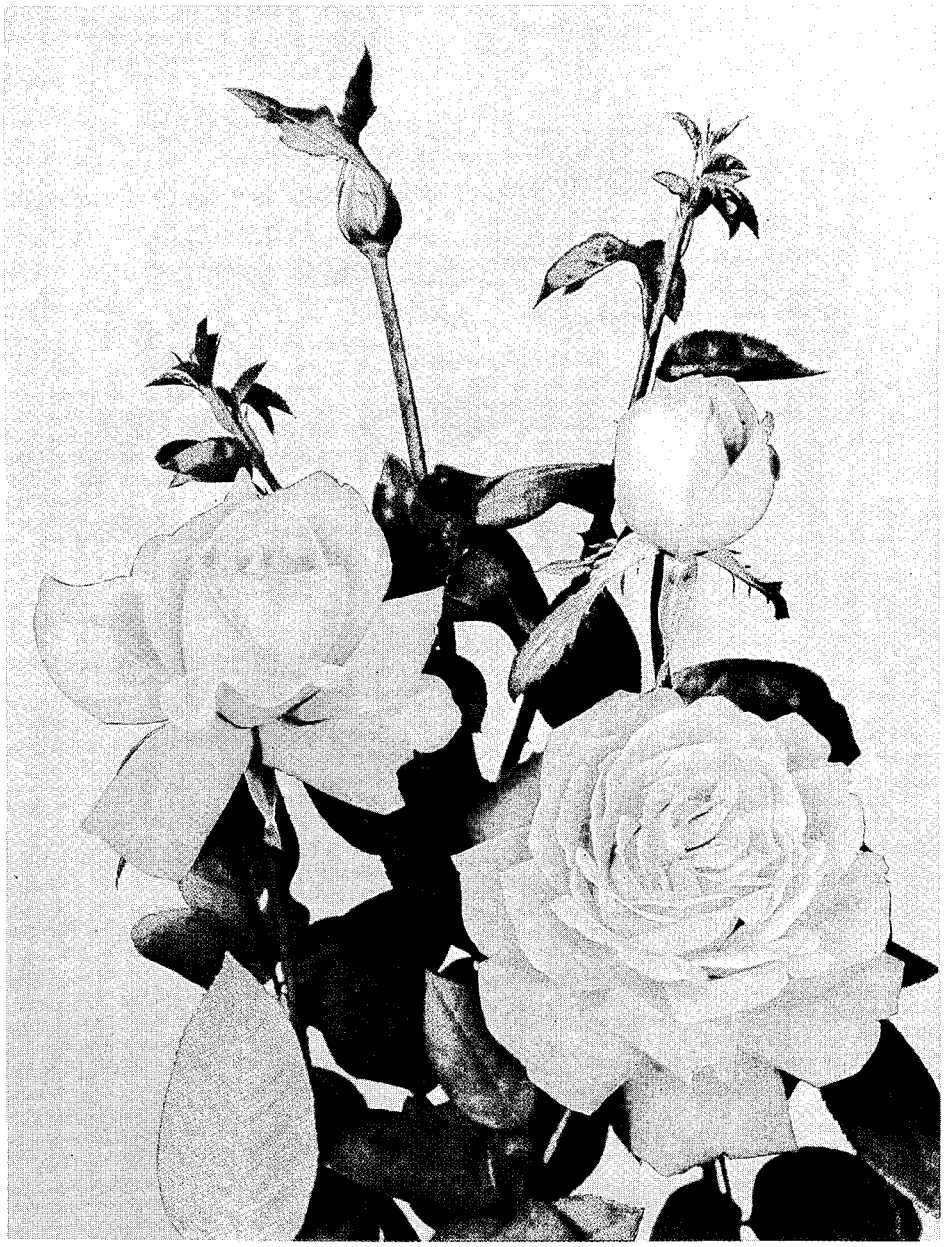
Inventor
H. C. Swim
By Robb & Robb
Attorneys Patented May 2, 1950

Plant Pat. 938

UNITED STATES PATENT OFFICE

938

ROSE PLANT

Herbert C. Swim, Ontario, Calif., assignor, by mesne assignments, to Inter-State Nurseries, Inc., Hamburg, Iowa, a corporation of Delaware Application March 8, 1949, Serial No. 80,305

1 Claim. (Cl. 47—61)

The present invention relates to a new and distinct variety of hybrid tea rose plant originated from the crossing of two well-known rose varieties, thereby combining a number of their good qualities and producing a much improved variety for cut flower and garden decoration.

This new variety possesses the following dominant novel and distinctive characteristics in combination:

(1) Unusual brilliance of the color of the flower, substantially as described and illustrated herein.

(2) Exceptional vigor of the plan for its type, which is bush hybrid tea, said vigor being, to the best of my knowledge, the equal of, or greater than, any other rose in this class now in commerce with respect to this characteristic.

(3) Large number of petals and the regularity of their placement and form, often giving the opening flower the appearance of a formal camellia bloom up to the point when it is three-quarters open.

(4) Abundance of the foliage and the continuity and abundance of the flowers, which characteristics, added to the above, giving this variety unusual value as a combination of garden decorative variety and an exhibition variety.

This new variety is distinct from its seed parent "Christopher Stone" (unpatented), for the following reasons:

(1) It is much more vigorous than "Christopher Stone," growing to at least twice and often three times the size of its seed parent.

(2) The color of the flowers in this new variety would be popularly described as crimson, whereas the flowers of "Christopher Stone" are scarlet.

(3) This new variety has at least twice as many petals as "Christopher Stone," and is therefore better suited to exhibition use than is "Christopher Stone."

This new variety differs from its pollen parent, "Charlotte Armstrong" (Pl. Pat. No. 455), in the following ways:

(1) Whereas "Charlotte Armstrong" is characterized by having many large and many small prickles, this new variety is best described as having several large and several small prickles, a distinction which is quite marked on visual observation.

(2) The leaves of this new variety are a darker green color than those of its seed parent, and have greater width in proportion to the length than is found in the leaves of "Charlotte Armstrong."

(3) The flowers of this new variety have many more petals than "Charlotte Armstrong," the flower buds are shorter in length in proportion to width and the color of the flower is a deeper red than is characteristic of its pollen parent.

(4) This new variety is more compact in growth habit than its pollen parent and for this reason, as well as because of its more abundant foliage, it is somewhat better adapted to garden decoration than "Charlotte Armstrong."

Asexual reproduction of this new variety shows the foregoing characteristics come true to form and are established.

The accompanying drawing illustrates the distinctive characteristics of the flowers at different stages of development from bud to full blown blossoms.

The following is a detailed description of the new variety, color terminology being in accordance with Horticultural Colour Chart of Robert F. Wilson, 1938, with exceptions noted from Ridgway's Color Standards and Nomenclature:

Type: Tall; bush; outdoor; seedling; for cut flowers and garden decoration.

Class: Hybrid tea.

Breeding: Seedling.

*Seed parent.*—"Christopher Stone" (unpatented).

*Pollen parent.*—"Charlotte Armstrong" (Pl. Pat. No. 455).

Propagation: Holds its distinguishing characteristics through succeeding propagations by budding (the only method used up to this time).

*Flower*

Locality where asexually reproduced by budding and grown: Ontario, California.

Flowers borne: Usually singly, sometimes two to three or more to stem; in irregular cluster; on strong, medium to long stems.

Quantity of bloom: Abundant; outdoors.

Continuity: Continuous during growing season.

Fragrance: Slight; tea.

Bud:

*Peduncle.*—Average length to long; average caliper to heavy; erect; usually rough because of numerous gland-tipped cilia and numerous small prickles. *Color.*—Biscay Green, Plate XVII (Ridgway).

*Before calyx breaks.*—*Size*—medium. *Form*—medium length; pointed; ovoid; with foliaceous appendages and bloom on the surface of the bud; with much cut foliaceous parts extending beyond the tip of the bud equal to ½ or more of its length.

*As calyx breaks.*—*Color*—between Chrysanthemum Crimson, Plate 824/3, page 169, and Erythrite Red, Plate 0027, page 190.

*Sepals.*—Inner surface with tomentum; margins of exposed sepals have gland-tipped cilia, while covered margins have woolly tomentum.

*As first petal opens.*—*Size*—average. *Form*—pointed to ovid. *Color*—outside—Crimson, Plate 22/1, page 22, with small area of Aureolin, Plate 3/1, page 3, at point of attachment; inside—between Rose Madder, Plate 23/1, page 23, and Rose Madder, Plate 23, page 23, with Aureolin, Plate 3/1, page 3, at point of attachment.

*Opening.*—Opens up well. It is not retarded from opening by cold, hot or dry weather.

Bloom: Size, when fully open—average to large; 3 inches to 4 inches.

*Petalage.*—Very double; from 60 to 70 petals, plus 8 to 14 petaloids; arranged regularly except at center.

*Form.*—High centered at first; becoming open to high centered; petals at first with tips reflexed outward; petals becoming later at maturity somewhat flat.

Petals:

*Texture.*—Moderately soft; with inside slightly velvety and outside satiny.

*Shape.*—Outside—broadly obovate, usually with one notch. Intermediate—obovate; apex with usually one to two notches. Inside—narrowly obovate; slightly irregular margins with apex rounded to flat.

*Color.*—Colors may be modified by being veined, overlaid or tipped with other colors.

This description of a newly opened flower was made from a rose grown outdoors in the month of September, at Ontario, California:

*Color.*—*Outside petal*—outside surface: Tyrian Rose, Plate 24/2, page 24, with small area near attachment region of Canary Yellow, Plate 2/2, page 2; inside surface: Tyrian Rose, Plate 24/1, page 24, with small area near attachment region of Aureolin, Plate 3/2, page 3. *Intermediate petal*—outside surface: Tyrian Rose, Plate 24/2, page 24, with small area near attachment region of Canary Yellow, Plate 2/2, page 2; inside surface: Rose Madder, Plate 23, page 23, with small area near attachment region of Aureolin, Plate 3/2, page 3. *Inner petal*—outside surface: between Rose Madder, Plate 23/2, page 23, and Rose Madder, Plate 23/1, page 23, with small area near attachment region of Canary Yellow, Plate 2/2, page 2; inside surface: Rose Madder, Plate 23, page 23, with small area near attachment region of Canary Yellow, Plate 2/2, page 2.

This description was made from a rose that was open for three days outdoors in the month of September, at Ontario, California:

*Color.*—*Outside petal*—outside surface: Tyrian Rose, Plate 24/2, page 24, with basal region of Canary Yellow, Plate 2/3, page 2; inside surface: Rose Bengal, Plate 25/2, page 25, with veined markings of Rose Bengal, Plate 25/1, page 25, petal base region is Canary Yellow, Plate 2/2, page 2. *Inside petal*—outside surface: Rose Madder, Plate 23/1, page 23, with vegetative streak from basal region toward petal apex of Canary Yellow, Plate 2/3, page 2, to near white; inside surface: Rose Madder, Plate 23, page 23, with area near attachment region of Canary Yellow, Plate 2/2, page 2.

*General color effect.*—Newly opened flower—Tyrian Rose, Plate 24/1, page 24. Three days open—Rose Madder, Plate 23/1, page 23, with the vegetative streak on inner petals clearly showing; vegetative streak, Canary Yellow, Plate 2/3, page 2, to near white.

*Behavior.*—Drop off cleanly; fading to Tyrian Rose, Plate 24/3, page 24; affected by hot, dry weather, as follows: tips of petals burn, becoming dark.

*Flower longevity.*—On bush in garden—4 to 5 days in September—80° F. Cut roses grown outdoors kept at livingroom temperatures—3 to 7 days in October.

*Reproductive organs*

Stamens: Average number; arranged regularly about pistils, a few mixed with petaloids.

Filaments: Medium length; ⅜″ long; lower portion of Claret Rose, Plate 021, page 109; upper portions of Aureolin, Plate 3/2, page 3; most with anthers.

Anthers: Medium size; all open at once approximately. *Color*—outside margins of Buttercup Yellow, Plate 5, page 5, older anthers tipped with Claret Rose, Plate 021, page 109; inside portion of Lemon Yellow, Plate 4, page 4.

Pollen: Abundant. *Color*—Buttercup Yellow, Plate 5/2, page 5.

Pistils: Many; approximately 120 in number.

Styles: Uneven; average length; thin; bunched. *Color*—Rose Opal, Plate 022, page 110.

Stigma: A dull greyish translucent white.

Ovaries: Most protruding from calyx.

Hips: Do not set readily on young plants and none were available for description.

Sepals: From newly opened flower—permanent; long; spear-shaped; recured. *Color*—Inside: Parrot Green, Plate VI (Ridgway), overlaid with a white tomentum; outside: Biscay Green, Plate XVII (Ridgway).

Seed: None available.

*Plant*

Foliage:

*Leaves.*—Compound of usually 3 to 5 leaflets; very abundant; medium size to large.

*Leaflets.*—Ovate with apex acute; base round; margin serrate at base, doubly serrate approaching tip.

*Color.*—Mature—upper surface: Parsley Green, Plate 00962/1, page 193; under surface: Asphodel Green, Plate XLI (Ridgway). *Young*—upper surface: Spinach Green, Plate 0960/3, page 187, in basal and central midrib region changing to Claret Brown, Plate I (Ridgway) in exterior regions; under surface: Corinthian Purple, Plate XXXVIII (Ridgway), changing to Clear Fluorite Green, Plate XXXII (Ridgway) along midrib.

*Rachis.*—Heavy; upper side grooved with stipitate glands on edges; under side with a few prickles and with stipitate glands.

*Stipules.*—Medium length; medium width; with medium-length points turning out at an angle of more than 45°, recurved toward the stem.

*Disease.*—More than average resistant to mildew.

Growth:

*Habit.*—Bushy; upright; spreading; much branched.

*Growth.*—Very vigorous.

*Canes.*—Moderately heavy.

*Main stems.*—*Color*—Oil Green, Plate V (Ridgway). *Large prickles*—several; medium length; hooked slightly downward; with medium-length narrow base. *Color*—varying from Russet, Plate XV (Ridgway) to Brick Red, Plate XIII (Ridgway). *Small prickles*—several. *Color*—Russet, Plate XV (Ridgway). *Hairs*—none.

*Branches.*—*Color*—Courge Green, Plate XVII (Ridgway). *Large prickles*—several; medium length; hooked slightly downward; with medium-length narrow base. *Color*—Bordeaux, Plate XII (Ridgway), tipped with Chalcedony Yellow, Plate XVII (Ridgway). *Small prickles*—several. *Color*—Bordeaux, Plate XII (Ridgeway), tipped with Chalcedony Yellow, Plate XVII (Ridgway). *Hairs*—none.

*New shoots.*—*Color*—Apple Green, Plate XVII (Ridgway). *Large prickles*—several; medium length; hooked slightly downward; with short, narrow base. *Color*—Vandyke Red, Plate XIII (Ridgway), with tip of Dresden Yellow, Plate 64/3, page 64. *Small prickles*—several. *Color*—Vandyke Red, Plate XIII (Ridgway), with tip of Dresden Yellow, Plate 64/3, page 64. *Hairs*—none.

I claim:

A new and distinct variety of rose plant, characterized as to novelty by the unusual brilliance of the color of the flowers; exceptional vigor for a plant of its type; the large number of petals and regularity of their arrangement which gives the appearance of a camellia bloom at one stage of development of the flower; abundance of the foliage; and continuity and abundance of the flowers, substantially as shown and described.

HERBERT C. SWIM.

No references cited.